United States Patent
Miller (10) Patent No.: US 7,963,900 B2
(45) Date of Patent: Jun. 21, 2011

(54) CENTRIFUGE LOADING PROCESS WITHIN AN AUTOMATED LABORATORY SYSTEM

(75) Inventor: Kerry Lynn Miller, Elkton, MD (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 449 days.

(21) Appl. No.: 12/142,500

(22) Filed: Jun. 19, 2008

(65) Prior Publication Data

US 2009/0318276 A1 Dec. 24, 2009

(51) Int. Cl.
*B04B 13/00* (2006.01)

(52) U.S. Cl. .............................. 494/37; 436/45; 494/20

(58) Field of Classification Search .............. 494/10–11, 494/16–21, 31, 37; 436/45; 422/67, 72
See application file for complete search history.

(56) References Cited

U.S. PATENT DOCUMENTS

| | | | |
|---|---|---|---|
| 3,151,073 A * | 9/1964 | Anthon ............................. | 494/1 |
| 4,805,469 A | 2/1989 | Commarmot | |
| 5,087,423 A | 2/1992 | Ishibashi | |
| 5,178,834 A | 1/1993 | Kagayama et al. | |
| 5,209,903 A | 5/1993 | Kanamori et al. | |
| 5,623,415 A | 4/1997 | O'Bryan et al. | |
| 5,730,697 A * | 3/1998 | Auchinleck ..................... | 494/20 |
| 5,876,670 A | 3/1999 | Mitsumaki et al. | |
| 6,019,945 A | 2/2000 | Ohishi et al. | |
| 6,060,022 A | 5/2000 | Pang et al. | |
| 6,117,392 A | 9/2000 | Hanawa et al. | |
| 6,117,683 A | 9/2000 | Kodama et al. | |
| 6,290,907 B1 | 9/2001 | Takahashi et al. | |
| 6,581,012 B1 | 6/2003 | Aryev et al. | |
| 6,599,749 B1 | 7/2003 | Kodama et al. | |
| 6,758,803 B2 * | 7/2004 | Jang .............................. | 494/10 |
| 7,115,090 B2 * | 10/2006 | Lagarde ......................... | 494/10 |
| 7,195,737 B2 * | 3/2007 | Itoh ............................... | 422/72 |
| 7,338,803 B2 * | 3/2008 | Mizzer et al. .................. | 436/45 |
| 2004/0184959 A1 | 9/2004 | Itoh | |
| 2007/0020764 A1 | 1/2007 | Miller | |
| 2009/0318276 A1 * | 12/2009 | Miller ............................ | 494/20 |

* cited by examiner

*Primary Examiner* — Charles E Cooley
(74) *Attorney, Agent, or Firm* — Leland K. Jordan (57) ABSTRACT

A scheduling process for loading samples into two or more centrifuges in a loading scheme that reduces the time required for high priority sample to be centrifuged. One centrifuge is initially loaded to about one-half of capacity and samples processed while the remaining centrifuge is loaded to full capacity before being operated. This creates a time-shift in the operational status of the two centrifuges so that a high-priority sample may advantageously be shuttled to whichever of the two centrifuges will be first-fully loaded and thus next-operated.

3 Claims, 12 Drawing Sheets

CENTRIFUGE LOADING PROCESS WITHIN AN AUTOMATED LABORATORY SYSTEM

FIELD OF THE INVENTION

The present invention relates to an automated clinical sample treatment and transportation system with one or more independent analytical stations having samples supplied thereto by a conveyor after being processed one of at least two centrifuges. More particularly, the present invention relates to a centrifuge loading process that enables high-priority samples to be centrifuged in a centrifuge that minimizing delays arising from other samples already loaded for centrifugation.

BACKGROUND OF THE INVENTION

A wide variety of automated chemical analyzers are known in the art and are continually being improved to increase analytical menu and throughput, to reduce turnaround time, and to decrease requisite sample volumes. These analyzers conduct assays using reagents to identify analytes in biological fluid samples such as urine, blood serum, plasma, cerebrospinal liquids and the like. For convenience and safety reasons, these fluid samples almost universally contained in capped sample tubes. The assay reactions generate various signals that can be manipulated to determine the concentration of analyte in the sample. See for example, U.S. Pat. Nos. 7,101,715 and 5,985,672 and assigned to the assignee of the present application and incorporated herein by reference. Improvements in analyzer technology, however, may be hampered if sufficient corresponding advances are not made in pre-analytical sample preparation and handling operations like sorting, batch preparation, centrifugation of sample tubes to separate sample constituents, cap removal to facilitate fluid access, and the like.

To address this need, commercial automated pre-analytical sample preparation systems, called Laboratory Automation Systems (LAS), have been developed to automatically transport sample in tubes to a number of pre-analytical sample processing stations that have been "linked together" like described in U.S. Pat. Nos. 6,984,527 and 6,442,440, both incorporated herein by reference. These LAS handle a number of different patient specimens contained in standard, bar code-labeled, evacuated tubes. The bar code label contains an accession number coupled to demographic information that is entered into a hospital's Laboratory Information System (LIS) along with test orders and other desired information. An operator places the labeled tubes onto the LAS system which automatically sorts and routes samples to the requisite processing devices for pre-analytical operations like centrifugation, decapping, and aliquot preparation prior to the sample being subjected to analysis by one or more analytical stations also "linked" to the LAS.

For certain clinical assays, plasma, obtained from whole blood by centrifugation, is used in the analysis. To prevent clotting, an anticoagulant such as citrate or heparin is added to the blood specimen immediately after it is originally obtained or the anticoagulant is placed in an empty blood collection tube prior to the patient sample being obtained. The specimen may then be centrifuged at a later time to separate plasma from blood cells.

For some biochemical laboratory tests, plasma and blood serum can be used interchangeably. Serum resembles plasma in composition but lacks the coagulation factors as serum is obtained by allowing a blood specimen to clot prior to centrifugation. For this purpose, a serum-separating tube may be used which contains an inert catalyst (glass beads or powder) to facilitate clotting as well as a portion of gel with a density designed to take up a location between the liquid and cellular layers in the tube after centrifugation, making separation more convenient. However, the anticoagulants in plasma can interfere with certain analytical results on serum.

Coagulation tests diagnosis hemorrhagic conditions such as hemophilia, where one or more of the twelve blood clotting factors may be defective, require all clotting factors to be preserved. A citrated evacuated blood collection tube is usually used, as the anticoagulant effects of citrate is dependent upon concentration and can be reversed for testing. Serum, therefore, is therefore inappropriate for coagulation tests.

From the above, it can be seen that analytical tests may be performed on whole blood, plasma or serum, and that sometimes either plasma or serum may be used. Thus, different centrifugation processes may be required for different patient samples depending upon which clinical tests are to be performed by which analytical stations. Differential spin rates and lengths of time are examples of variables that make up what are hereinafter termed "centrifuge protocols" for different samples. For purposes of processing efficiency, when incoming samples are placed into an LAS, it is a general practice to set aside and "batch-together" those samples that have the same centrifuge protocol requirement. At a convenient time, an available centrifuge is adjusted to operate with the operating parameters to provide the required centrifuge protocol and the batch of samples are processed as a group.

In general, centrifugation requires tens of minutes for cycling through a load of tubes by loading centrifuge baskets in a balanced pattern with blood samples taken from the LAS conveyor, spinning the loaded centrifuge baskets, unloading the processed tubes and returning them to the LAS conveyor. If all samples to be handled by an LAS are of routine priority, samples are processed in a first-in-first-out scheduling process. However, non-routine samples requiring a shortest possible turn-around-time (STAT) arise in emergency and surgical operations. STAT samples are consequently given the highest possible priority so as to require the shortest time between receipt and analytical result. STAT samples are identified during loading onto the LAS, are routed ahead of routine samples and are centrifuged per the requisite centrifuge protocol prior to being shuttled to an appropriate analyzer. An undesirable and unavoidable delay arises when the LAS centrifuge is set up for one centrifuging protocol and the STAT sample has a different centrifuging requirement; this requires that centrifugation of samples in the centrifuge be completed and unloaded and that the established protocol be changed to match the STAT sample's requirements. As disclosed in U.S. Ser. No. 11/448,287 incorporated herein by reference, this delay can be partially ameliorated by providing more than one centrifuge set up with different operating protocols. While this provides flexibility if different centrifuges are operated with different operating protocols, throughput may be adversely affected unless the incoming operating load or demand is balanced to match centrifuging capacities. In addition, for simplicity in managing the incoming stream of samples to be centrifuged, incoming samples are processed in the order in which they are introduced to the LAS with different centrifuges being evenly "fed" with samples to be processed. STAT samples are simply placed at the front of the line of incoming samples.

To resolve the difficulties associated with handling samples that require different centrifuge protocols and simultaneously providing accelerated pre-processing for high-priority STAT samples, an LAS having two centrifuges will batch together those samples having the same centrifuge requirements and send them alternately to the two centrifuges. When a STAT sample appears, it is transported to whichever of the two centrifuges can be unloaded must quickly and then the STAT sample is processed immediately if the centrifuge's operating conditions match the STAT sample's centrifuging protocol. If not, the centrifuge's operating conditions must be changed to match the STAT sample's centrifuging protocol and then the STAT sample may be properly centrifuged and conveyed to an appropriate analyzer.

U.S. Pat. No. 6,060,022 discloses a LAS that is operated as generally described above. The LAS has an input workstation, one or more analyzers, and an automated centrifuge for automatically processing multiple sample containers. The workstation includes multiple input locations for inputting sample containers with at least one location selected for high-priority samples. Only one centrifuge is employed, thereby introducing processing inefficiencies because of the relatively long time required for centrifuging. As discussed above, samples having similar centrifugation requirements are "staged together" and processed in serial batches until all are completed. STAT samples are placed at the front of the line of incoming samples but are not given any special priority as far as being centrifuge processing within a batch.

Although LAS have advanced the art of sample handling and processing, there remains the challenge of enabling STAT samples to be presented to a centrifuge processing station from the conveyor of an LAS in a scheduling order that minimizes delays from other samples scheduled to be processed by the same centrifuge. Because of the life-saving implications of even slightly reducing the time from receipt of an STAT sample until that STAT sample is made available to a clinical analyzer, such an improvement is highly desirable.

SUMMARY OF THE INVENTION

The present invention provides a scheduling process for loading samples into two or more centrifuges in a loading scheme that reduces the time required for high priority samples to be centrifuged. This is accomplished by initially loading a first centrifuge to less than full capacity and processing samples while the remaining second centrifuge is loaded to full capacity before being operated. Subsequently, both centrifuges are loaded to full capacity prior to being operated. As a result, there is a time-shift in the operational status of the two centrifuges so that a high-priority sample may advantageously be shuttled to whichever of the two centrifuges will be next-first-fully loaded and thus next-centrifuged. In particular, the present invention is a method for operating a laboratory automation system having a conveyor for transporting individual sample tubes from a sample loading/unloading station to either of at least two centrifuges by initially loading one of the centrifuges to a centrifuging capacity that is less than or about half of full centrifuging capacity, and operating and refilling this centrifuge. Meanwhile, at the same time initially loading a second centrifuge to full capacity and operating and refilling this centrifuge so that STAT samples may be supplied to whichever of the centrifuges is most closely refilled to full capacity.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
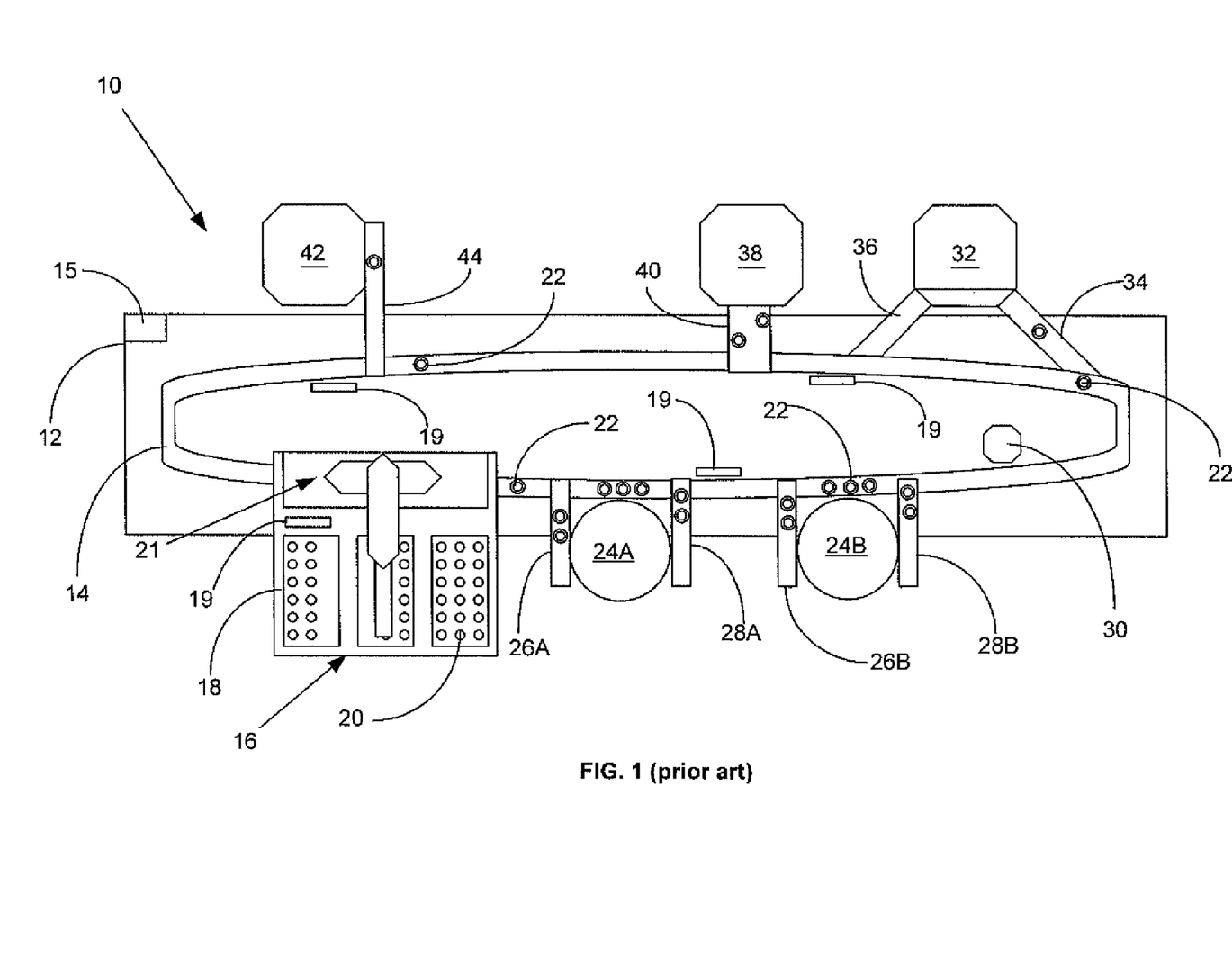
FIG. 1 is a simplified schematic plan view of a prior art automated sample handling system including a conveyor controlled in cooperation with several pro analysis sample treatment stations and analytical stations in which the present invention may be employed advantageously.

FIG. 1 shows an automated clinical laboratory sample handling LAS 10 capable of automatically pre-processing multiple sample containers 20, typically sample test tubes 20, contained in multiple-tube sample racks 18 prior to analysis by an analyzer 32, 38 or 42. Typically, specimens to be automatically processed are provided to laboratory automation system LAS 10 in capped containers 20. Each of the sample containers 20 is provided with identification indicia, such as a bar code, machine readable by a sensor 19 and indicating a patient's identification as well as the assay procedures to be accomplished upon the sample therein. The containers 20 are generally held in multiple-tube racks 18 that generally have additional identification indicia thereon.

LAS 10 comprises an operating base 12 upon which a belt-like conveyor track 14 transports individual sample tube containers 20 carried in sample container carriers 22 from a sample container loading/unloading station 16, having more than one multiple-tube rack 18, as well as a high-priority, STAT active input lane, to one of two automated centrifuges 24A and 24B. After being centrifuged, sample tube containers 20 are transported therefrom to an automated tube de-capper 30 for automatically removing caps from capped sample containers 20 and therefrom to one or more analyzers 32, 38, and 42 before returning the original sample tube containers 20 to the sample tube loading/unloading robotic station 16. It should be understood that more than three analyzers 32, 38, and 42 may be linked by conveyor track 14; for purposes of simplicity, only three are shown. A remote analyzer 43 may be serviced by LAS 10 even though the remote analyzer 43 is not directly linked to LAS 10, for instance by an independent robotic system. The sample handling LAS 10 has a number of sensors 19 for detecting the location of a sample tube container 20 by means of identifying indicia placed on or within each sample tube carrier 22. Conventional bar-code readers may be employed in such tracking operations.

Centrifuges 24A and 24B and each analyzer 38, 42 and 32 are generally equipped with various loading mechanisms 26A and 24B and 28, 40 and 44 or tracks 34 and 36, respectively, for removing a sample tube carrier 22 from track 14, moving the sample tube carrier 22 to and from centrifuges 24A and 24B, to and from or into and out from analyzers 38, 42 and 42, respectively. Alternately, sample tube containers 20 may be removed from a sample tube carrier 22 for such processing. Typically, the loading/unloading station 16 includes at least two X-Y-Z robotic arms 21 conventionally equipped with robotic clamping hands.

Sample handling LAS 10 is controlled by a conventionally programmed computer 15, preferably a microprocessor based central processing unit CPU 15, housed as part of or separate from the system 10 to control movement of the sample tube carrier 22 throughout LAS 10 whereat various types of assay processing occurs, as described below. CPU 15 controls sample handling system 10 according to software firmware, or hardware commands or circuits like those used on the Dimension® clinical chemistry analyzer sold by Siemens Healthcare Diagnostics Inc. of Deerfield, Ill., and are typical of those skilled in the art of computer-based electromechanical control programming.

The present invention may be implemented using a computer interface module CIM that allows for a user to easily and quickly access a variety of control screens and status information display screens that fully describe a plurality of inter-related automated devices used for sample preparation and clinical analysis of a patient's biological sample. Such a CIM preferably employs a first display screen that is directly linked to a plurality of additional display screens containing on-line information about the operational status of plurality of inter-related automated devices as well as information describing the location of any specific sample and the status of clinical tests to be performed on the sample. The CIM is thus adapted to facilitate interactions between an operator and automated clinical analytical system 10 wherein the module comprises a visual touch screen adapted to display a menu including icons, scroll bars, boxes and buttons through which the operator may interface with the clinical analytical system and wherein the menu comprises a number of function buttons programmed to display functional aspects of the clinical analytical system.

Figure 2:
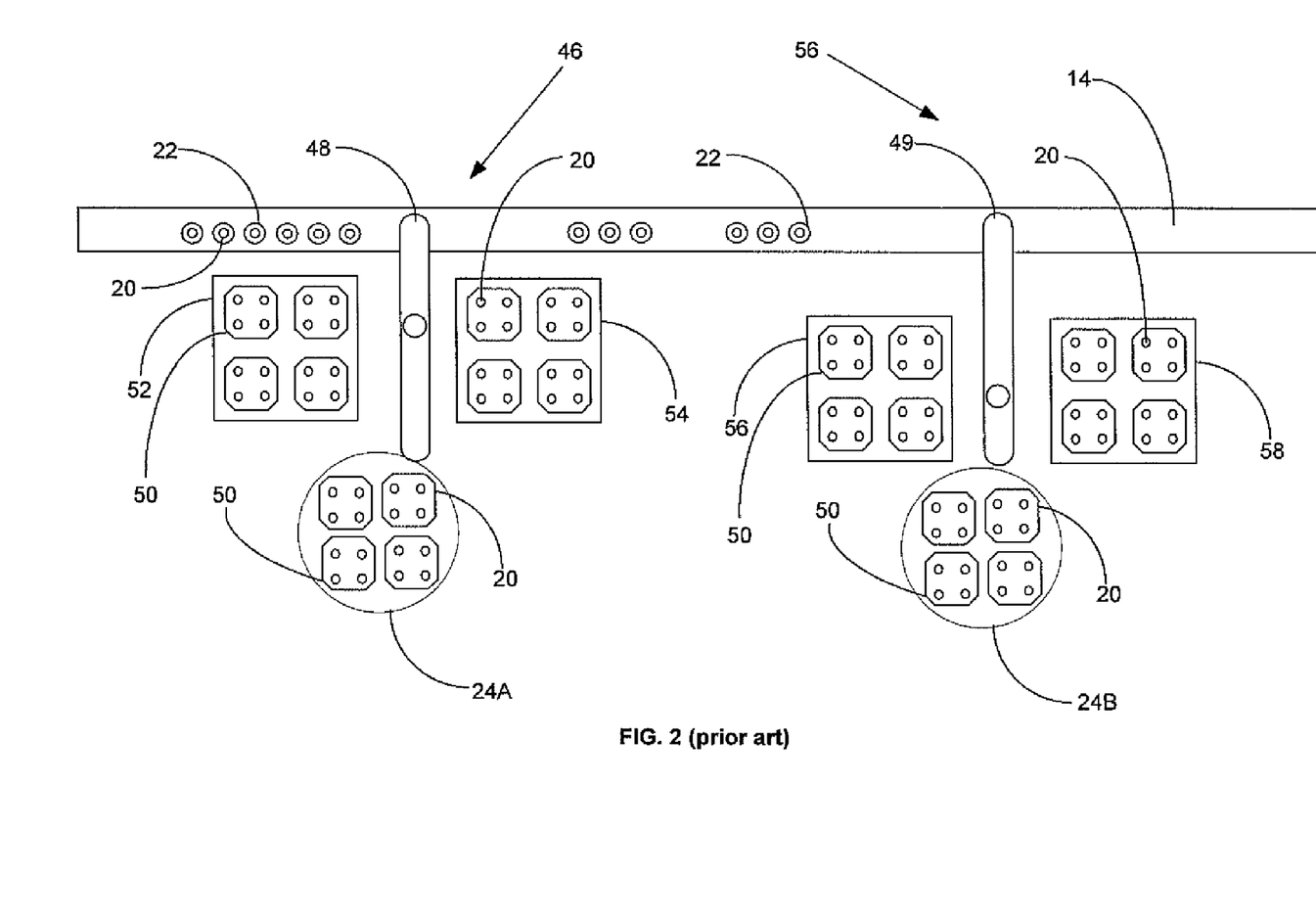
FIG. 2 is a simplified schematic plan view of two centrifuges in the automated sample handling system of FIG. 1.

FIG. 2 illustrates a typical centrifuge loading station 46, like those disclosed in U.S. Pat. No. 6,060,022 and U.S. Pat. No. 6,589,789, adapted to remove a sample tube 20 carried by a sample tube carrier 22 from track 14 and to place individual sample tubes 20 in a weight-balanced pattern into open receptacles (not shown for purposes of clarity) in a centrifuge bucket 50 disposed temporarily on a first bucket weighing and loading platform 52. Centrifuge loading station 46 is provided with a bucket transfer device 48 adapted to remove a weight-balanced centrifuge bucket 50 from first loading platform 52 and to place the weight-balanced centrifuge bucket 50 into centrifuge 24A for centrifuging. In order to avoid an unbalanced centrifuging condition, additional weight-balanced centrifuge buckets 50 are loaded on the first loading platform 52 placed into centrifuge 24A so as to maintain an overall balanced load within centrifuge 24A. Typically, centrifuge buckets 50 are placed into centrifuge 24A in opposing pairs. In addition, a bucket 50 may be artificially balanced by moving differently weighted sample tubes 20 into different open receptacles and/or by employing "dummy" tubes 20 having known weights therein.

After centrifuging is complete, centrifuge loading station 46 is even further provided with bucket transfer device 48 adapted to remove a centrifuge buckets 50 from centrifuge 24A one after another and to place each centrifuge bucket 50 onto a first bucket unloading platform 54. (For purposes of simplicity, only four sample tubes 20 are illustrated in each centrifuge bucket 50, while in practice a larger number on the order of ten-twenty sample tubes 20 are placed into each centrifuge bucket 50.) Finally, bucket transfer device 48 is adapted to remove centrifuged sample tubes 20 from centrifuge bucket 50 disposed on first bucket unloading platform 54 and to replace the now-centrifuged sample tubes 20 into carriers 22 onto track 14 for subsequent pre-analytical processing and/or for analysis. After all sample tubes 20 have been removed from a centrifuge bucket 50, the empty centrifuge bucket 50 is moved from unloading platform 54 onto loading platform 52 and the process is continued until all of the sample tubes 20 in sample carriers 22 in LAS 10 containing samples requiring some form of separation have been centrifuged and replaced onto conveyor track 14. FIG. 2 basically illustrates centrifuge loading station 46 with buckets 50 loaded with samples 20 removed from track 14 and awaiting centrifugation, buckets 50 loaded with samples 20 during centrifugation and buckets 50 loaded with samples 20 subsequent to centrifugation and ready to be replaced in sample tube carriers 22 on track 14. This process is known to and practiced by those skilled in the art, particularly those bucket loading operations that involve and require weight balancing of buckets 50. Terminology universally understood by those skilled in the art include phrases like "loaded", "balanced", "carrier", "bucket", "rotor", "insert" and "rack" and are used herein without detailed explanation.

The present invention is advantageously practiced in an LAS 10 having at least two centrifuges 24A and 24B, the second centrifuge 24B provided with a second centrifuge loading station 56 for handling sample tubes 20 carried by a sample tube carriers 22 in a manner similar to that described for loading and unloading centrifuge 24A. In this instance, the second centrifuge loading station 56 is adapted to remove a sample tube 20 from a sample tube carrier 22 on track 14 and to place individual sample tubes 20 in a weight-balanced pattern within a centrifuge bucket 50 disposed temporarily onto a second bucket loading platform 58 and to place the weight-balanced centrifuge bucket 50 into centrifuge 24B for centrifuging. As before, after centrifuging is complete, centrifuge loading station 56 is even further adapted to remove a centrifuge bucket 50 from centrifuge 24B and to place the centrifuge bucket 50 onto a second bucket unloading platform 60. Finally, centrifuge loading station 46 is adapted to remove a sample tube 20 from a centrifuge bucket 50 disposed on second bucket unloading platform 60 and to replace a now-centrifuged sample tubes 20 into a sample tube carrier 22 onto track 14 for subsequent processing.

Figure 3A:
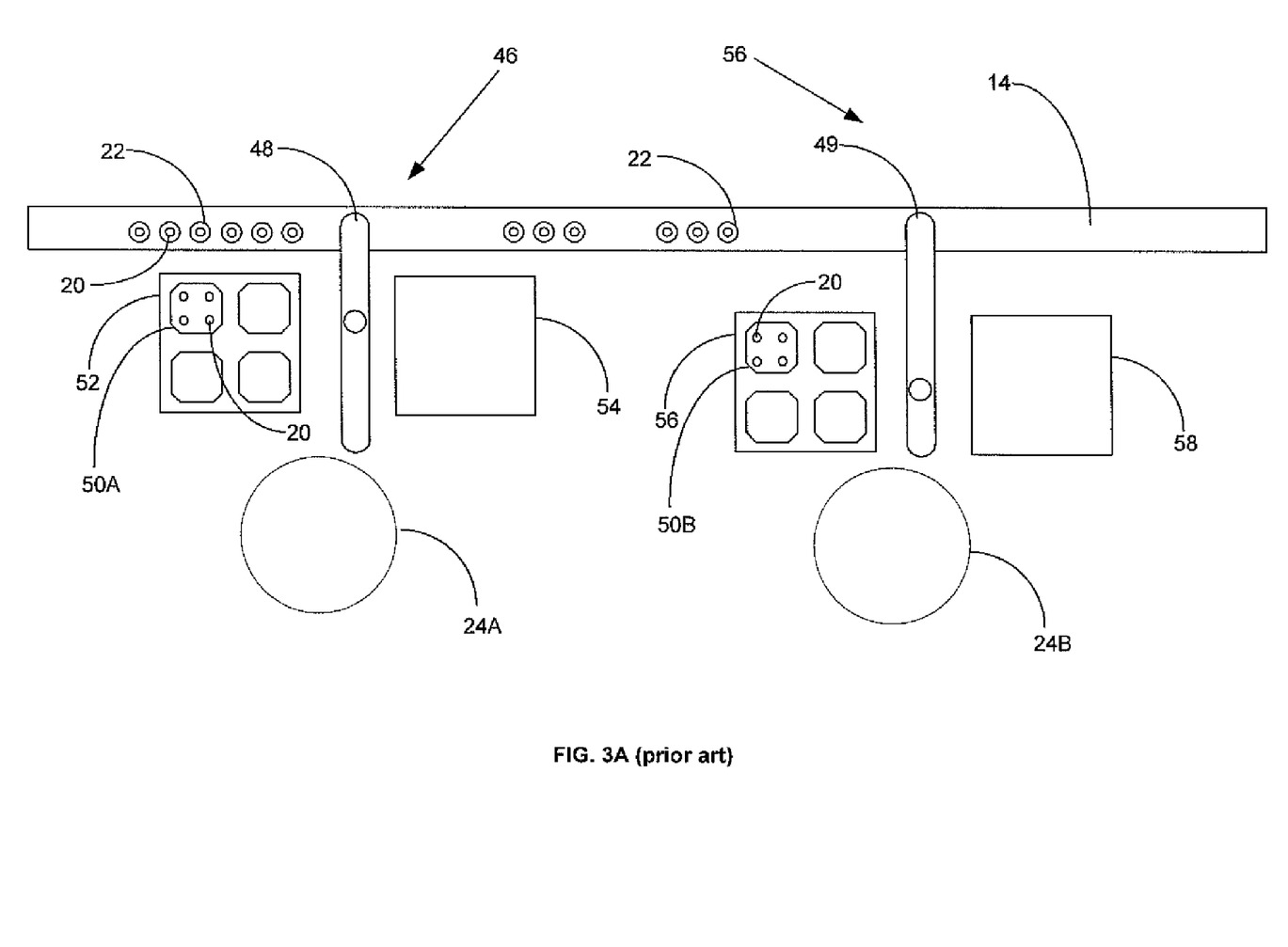
FIGS. 3A-3D are a simplified schematic plan view of a prior art centrifuge loading scheme for the two centrifuges in the automated sample handling system of FIG. 1.
Figure 3B:
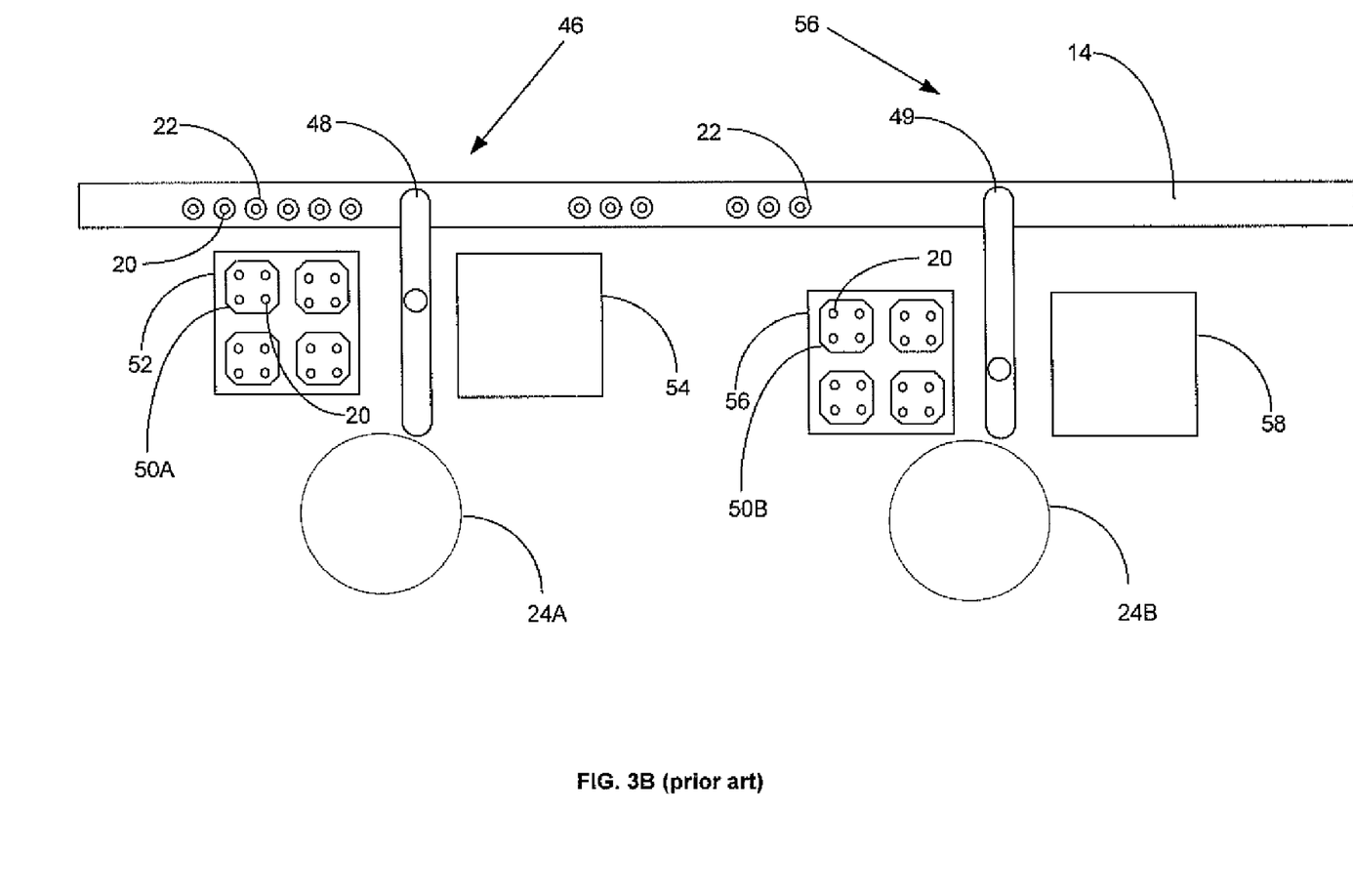
Figure 3C:
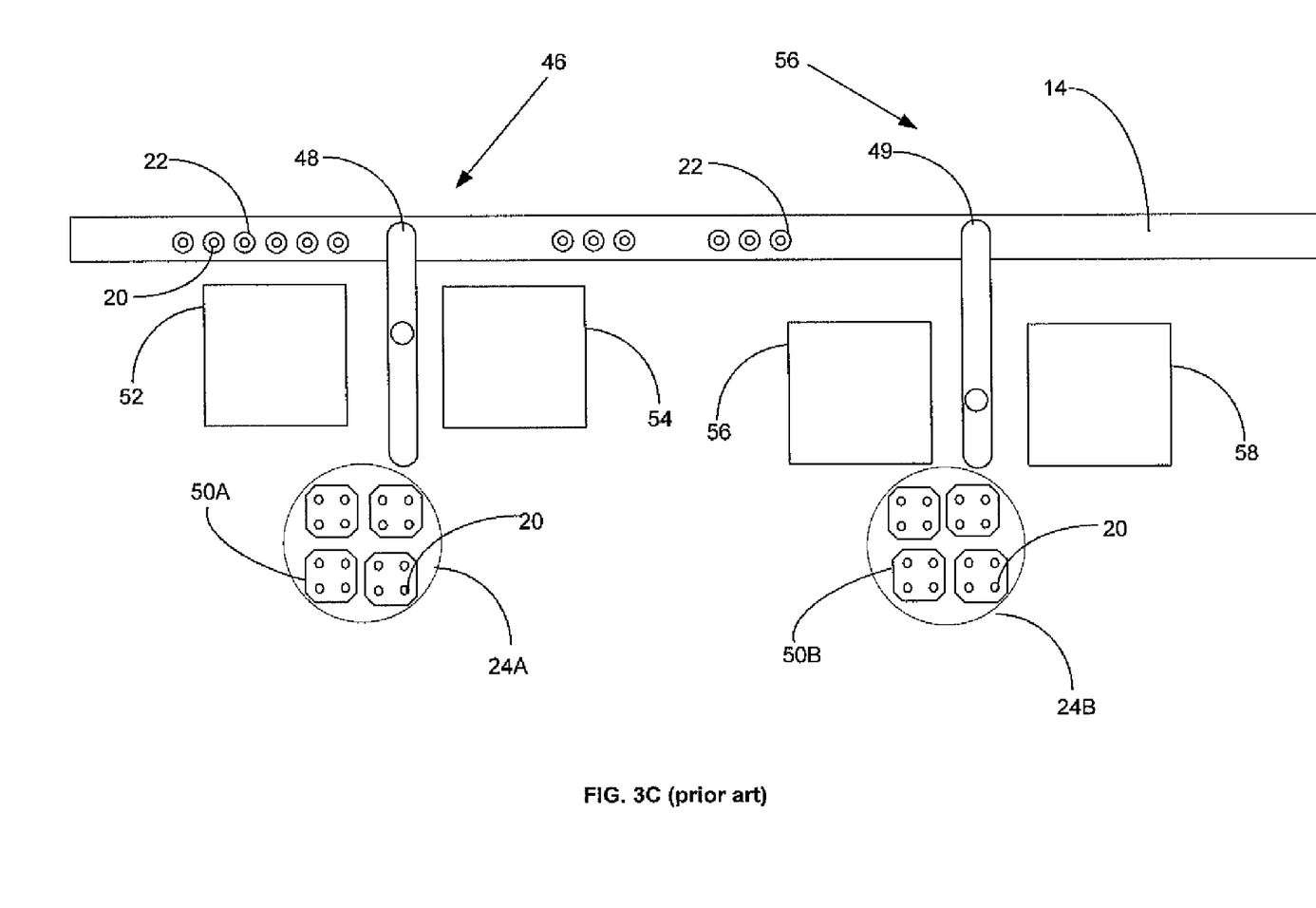
Figure 3D:
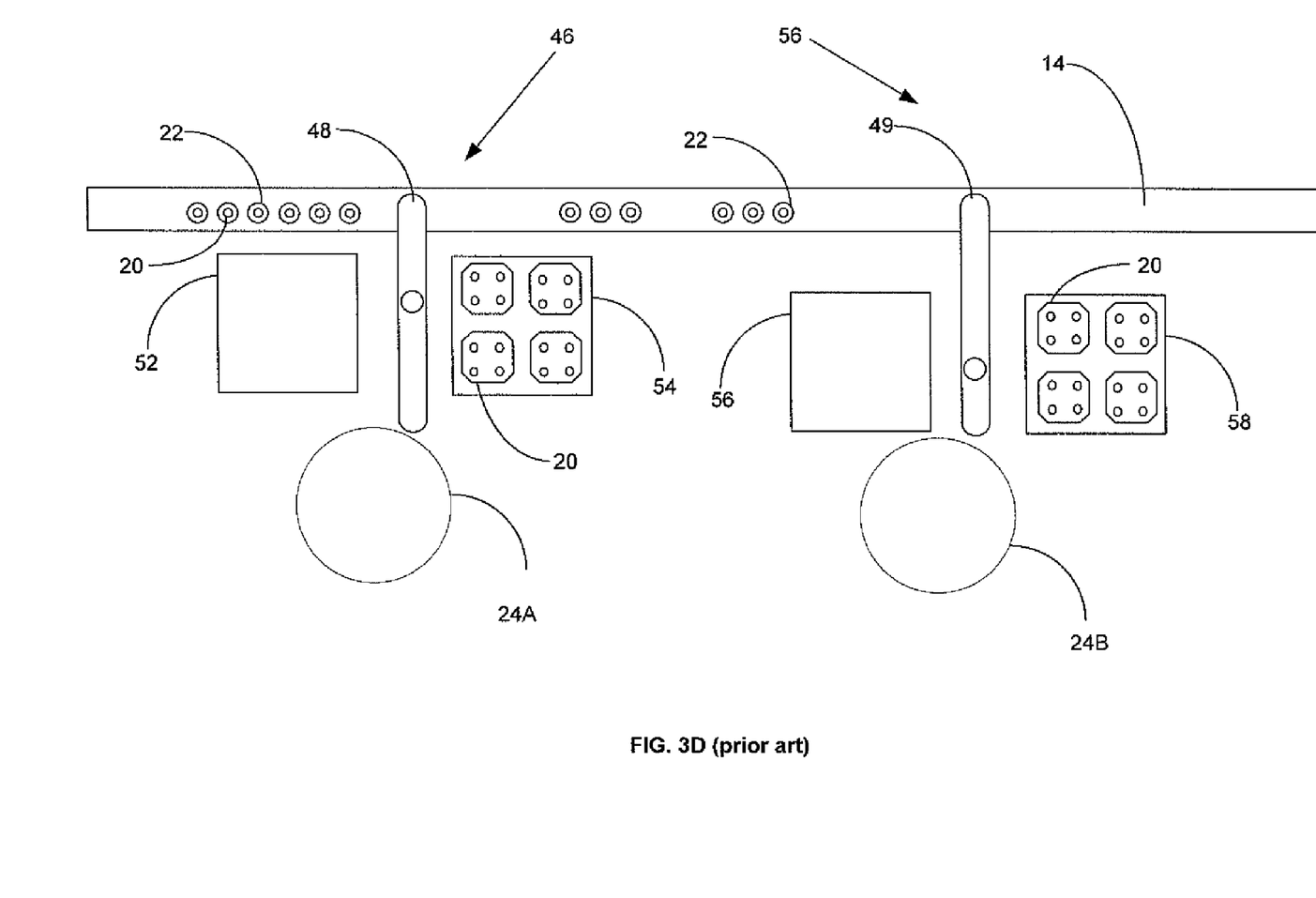

In the prior art, sample tubes 20 are presented to centrifuges 24A and 24B in an alternating pattern that begins when a "batch" of sample tubes 20 has been identified for processing within LAS 10. In such an alternating pattern, a first sample tube 20 is placed into a first bucket 50A on bucket loading platform 52 on centrifuge 24A and then a second sample tube 20 is placed into a bucket 50B on bucket loading platform 58 on centrifuge 24B. This process is continued, with "odd numbered" sample tubes 20 placed in a bucket 50A on bucket loading platform 52 on centrifuge 24A while "even numbered" sample tubes 20 are placed in a bucket 50 on bucket loading platform 58 on centrifuge 24B, until both buckets 50A and 50B are fully loaded as illustrated in FIG. 3A. As described above and seen in FIG. 3B, This loading process continues with a "odd-numbered" sample tubes 20 being placed in the remaining centrifuge buckets 50 on bucket loading platform 52 on centrifuge 24A and "even-numbered" sample tubes 20 being placed in the remaining centrifuge buckets 50 on bucket loading platform 58 on centrifuge 24B, as illustrated in FIG. 3B. Subsequently, loaded centrifuge buckets 50 are placed into centrifuges 24A and 24B, as seen in FIG. 3C and the centrifuges are operated using their respective operating protocols. After the centrifuging protocols are completed, the buckets 50 are removed from centrifuges 24A and 24B and placed on bucket unloading platforms 54 and 58, as illustrated in FIG. 3D. Bucket loading procedures like this alternating "odd-even" scheme are employed in state of art laboratory automation because of an emphasis on increasing overall laboratory throughput. Although not shown, during the bucket handling process of FIGS. 3A-D, "empty" centrifuge buckets 50 on bucket loading platform 52 continue to be loaded with "odd-numbered" sample tubes 20 and "empty" centrifuge buckets 50 on bucket loading platform 58 on centrifuge 24B continue to be loaded with "even-numbered" sample tubes 20. However, a hospital laboratory must also be prepared to handle high-priority STAT (short-turn-around-time) samples and this is usually done by having dedicated STAT processing lines. This is a costly but effective, approach particularly when the alternative of a delayed test result for a critically ill patient is considered. The present invention embraces the needs of the laboratory and manages multiple priorities with minimal disruption to the processing of routine samples.

This prior art procedure for loading in an LAS with at least two centrifuges in an alternating pattern to their full capacity is used because of the simplicity of programming the operation of LAS 10, centrifuge loading stations 46 and 56 and centrifuges 24A and 24B. This practice works well as long as no high-priority, STAT sample tubes 20 are presented to LAS 10, and maintains a constant stream of centrifuged sample tubes 20 to be supplied to subsequent analytical devices. In the event, however, that a high-priority, STAT sample tube 20 is presented to LAS 10 for processing, it is also a common practice to place the high-priority, STAT sample tubes 20 into a high-priority, STAT active input lane from which a high-priority, STAT sample tube 20 can be immediately placed in a sample tube carrier 22 on conveyor track 14. While this practice reduces the time required to bring such a high-priority, STAT sample tube 20 to either of centrifuge 24A or 24B, the previously described pattern for alternating placement into a bucket 50 on bucket loading platform 52 and then on bucket loading platform 58 introduces an adverse time delay because neither one of the buckets 50 on bucket loading platform 52 and on bucket loading platform 56 may be nearing a fully loaded condition.

The present invention solves this dilemma and further reduces the time required to bring a high-priority, STAT sample tube 20 to either of centrifuge 24A or 24B by initially loading one of the two available centrifuges, 24A or 24B, with buckets 50 that have been loaded with less than the full capacity of each bucket 50. This is achieved using the previously described alternating "odd-even" sample tube 20 loading procedure.

Subsequent to this "less-than-full initial loading" of, for example, centrifuge 24A, the previously described alternating placement of sample tubes 20 into bucket 50C on bucket loading platform 52 and continuing into bucket 50B on bucket loading platform 58, is resumed. FIG. 4B illustrates four of such sample tubes 20 loaded into opposed buckets 50A and 50C on bucket loading platform 52 and four of such sample tubes 20 loaded into bucket on bucket loading platform 58. At this stage, opposed buckets 50A and 50C may optionally be transferred to centrifuge 24A (FIG. 4C) and the centrifuging process begun; alternately, the previously described alternating "odd-even" sample tube 20 loading procedure may be continued until all four buckets 50A, 50C, 50D and 50E are loaded to a "less-than-full loading" condition prior to being transferred to centrifuge 24A as shown in FIG. 4D and after being transferred to centrifuge 24A, centrifuge 24A may be operated at this "less-than-fully load" condition (FIG. 4E). During the loading of buckets 50 on bucket loading platform 52, the previously alternating "odd-even" sample tube 20 loading procedure of buckets 50B, 50F, 50G and 50H on bucket loading platform 58 is continued as indicated in FIG. 4D.

The important advantage of initially loading buckets 50A and 50C of centrifuge 24A to this "less-than-full" condition as taught by the present invention can produce as much as a 50% reduction in STAT turn-around time in the instance that both centrifuges 24A and 24B are both fully loaded when a STAT sample is presented for processing. As explained below, this is achieved by loading a high-priority sample tube 20 into whichever centrifuge bucket 50 will be next placed into centrifuge 24A or 24B.

Figure 4A:
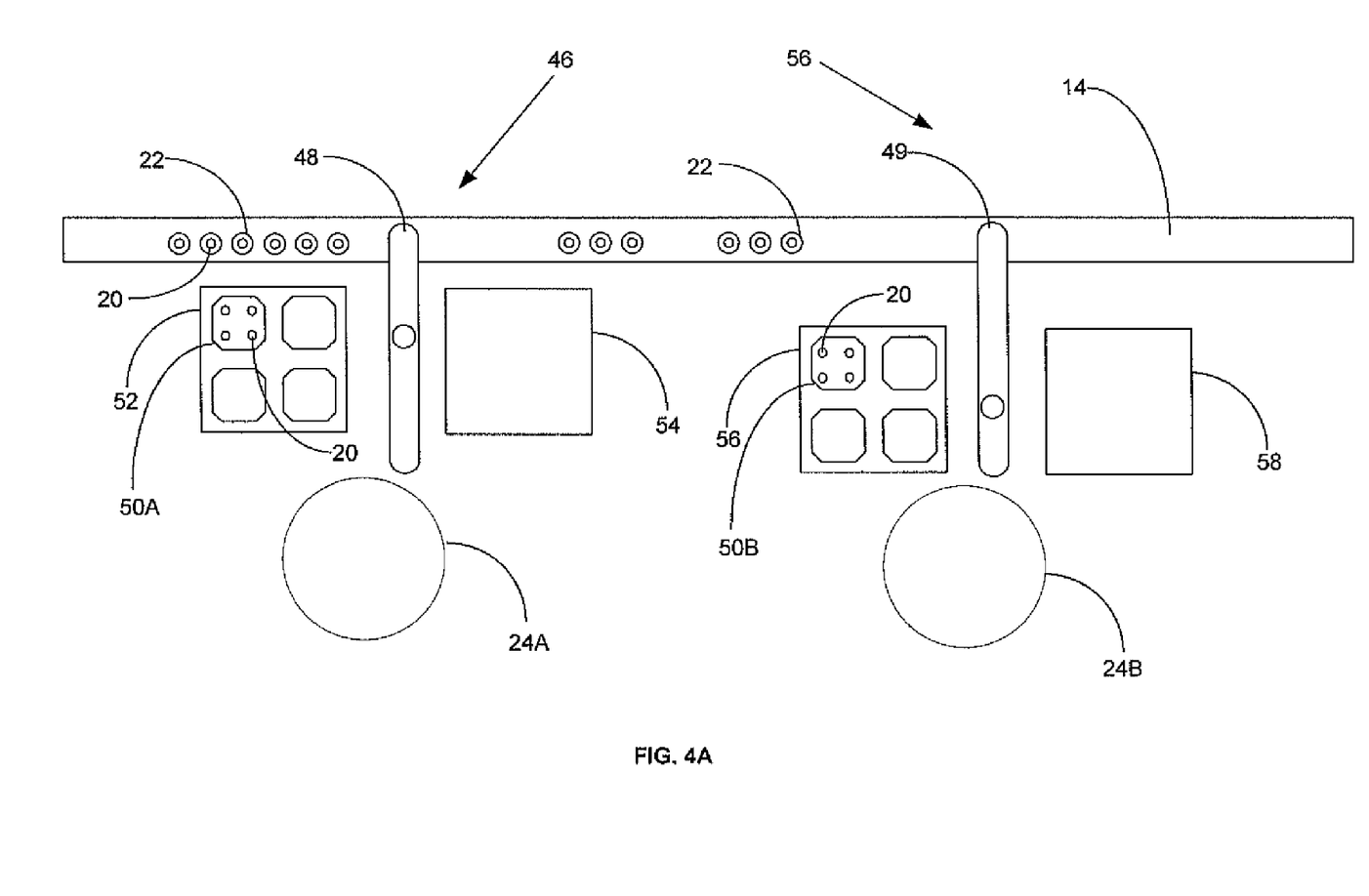
FIGS. 4A-4D are a simplified schematic plan view of the scheme of the present invention for loading samples into the two centrifuges in the automated sample handling system of FIG. 1.
Figure 4B:
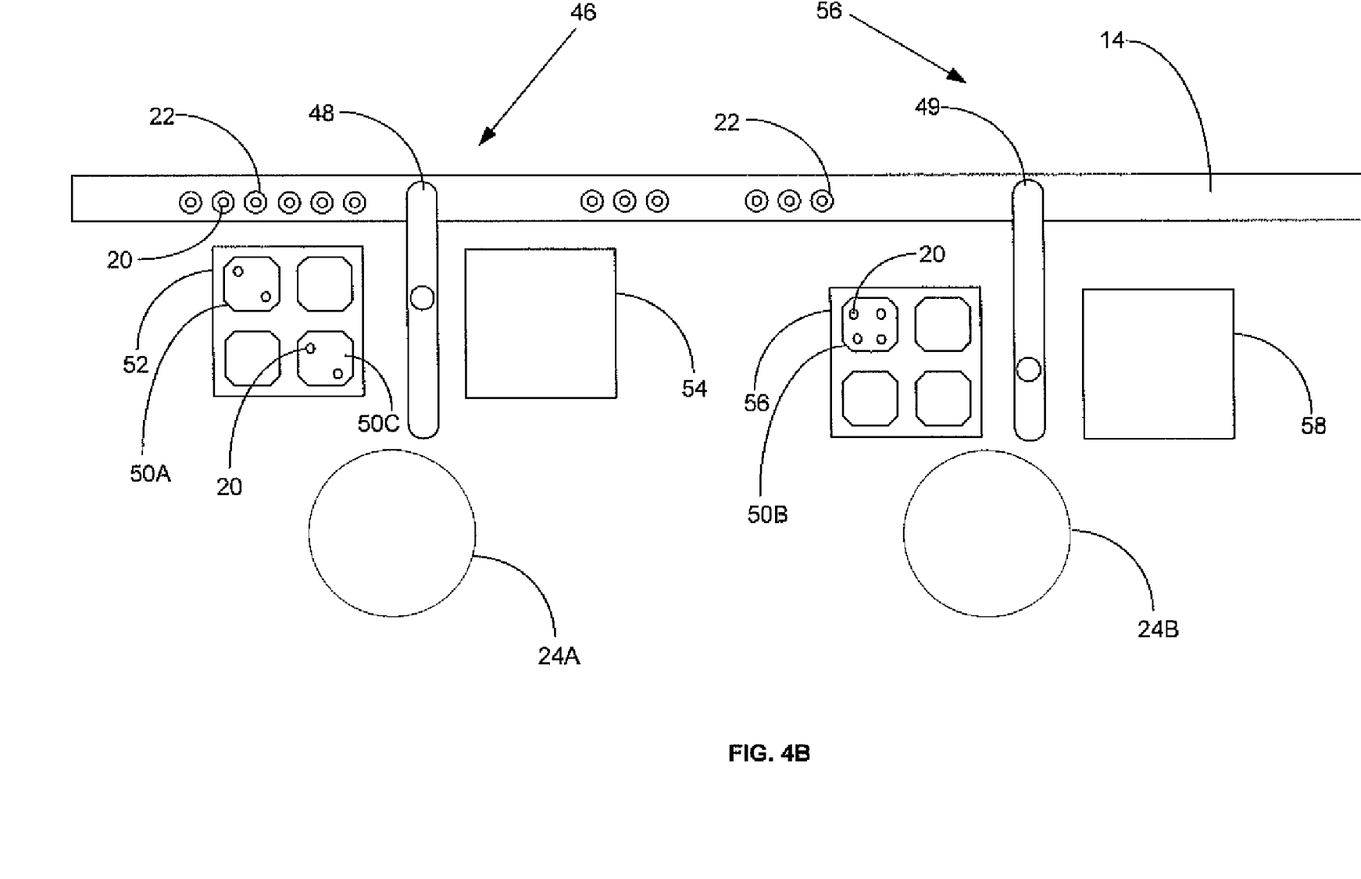
Figure 4C:
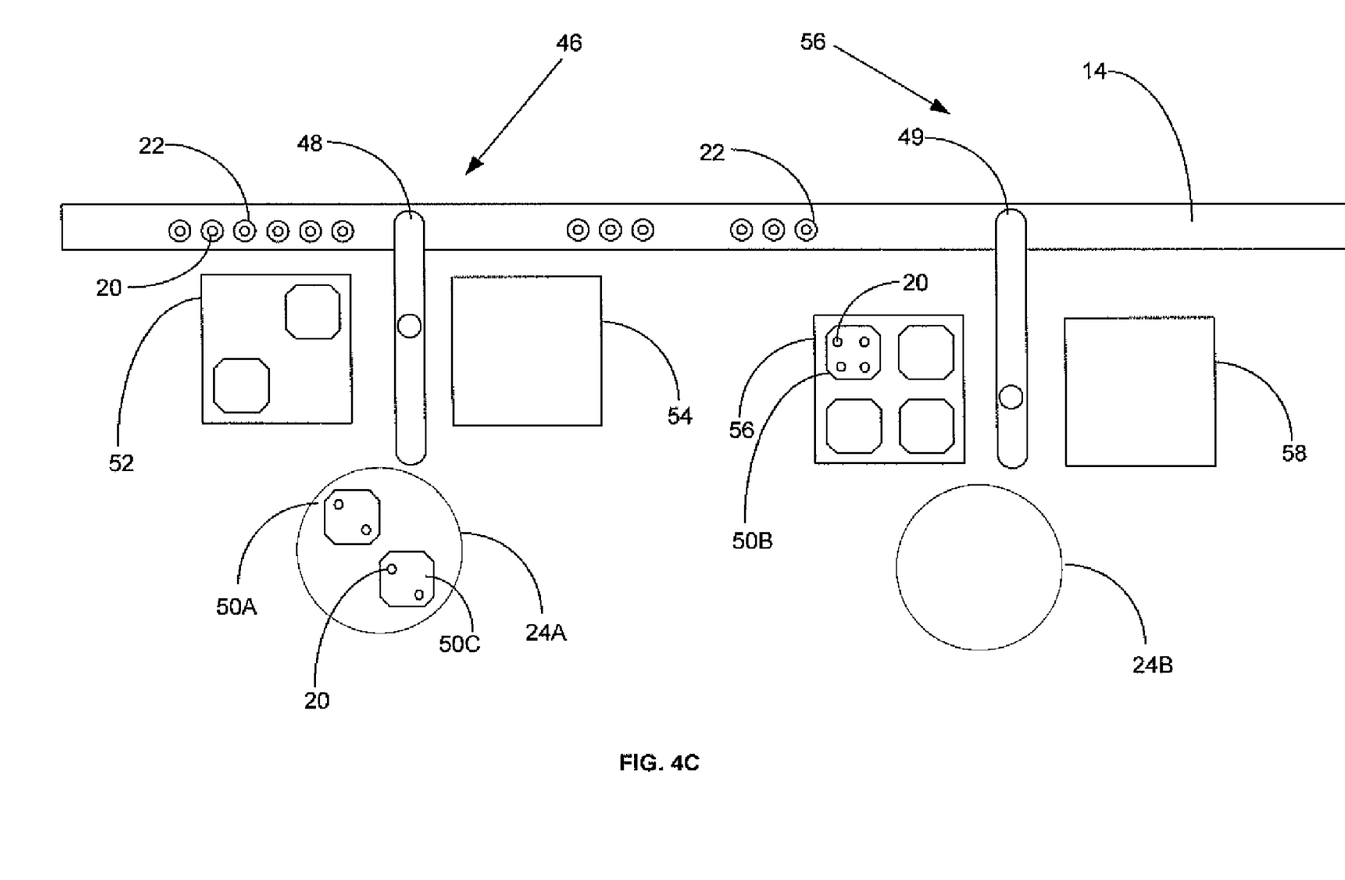
Figure 4D:
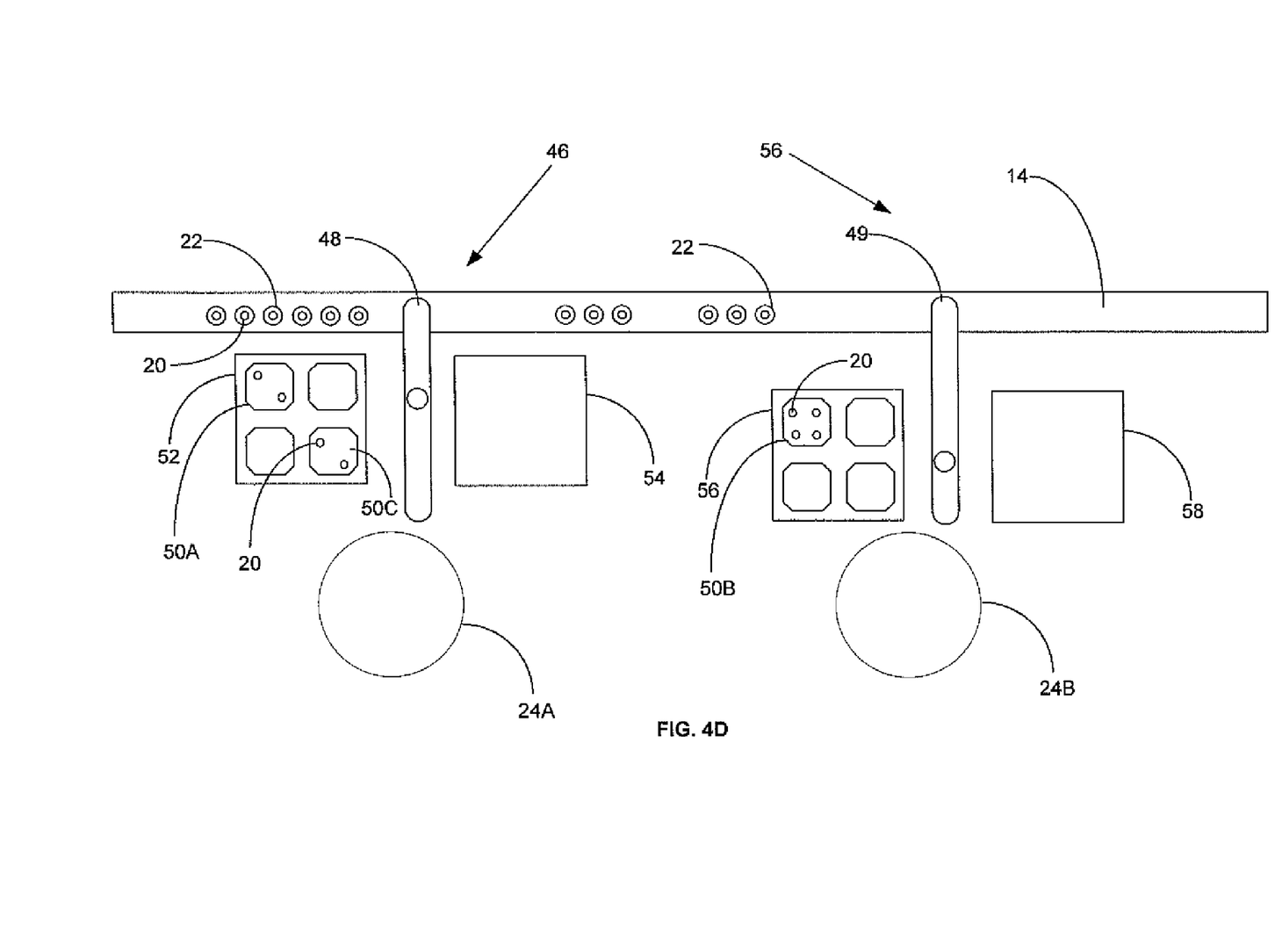

In the centrifuge loading scheme of the present invention like illustrated in FIGS. 4-4F, whenever a STAT sample appears, the STAT sample may advantageously be shuttled to which ever of the two centrifuges 24A or 24B is in a most closely filled situation. Because the initial loading of the first centrifuge 24A was done in a manner that allowed centrifuging of the "less-than-full loaded" buckets 50A-C-D-E to begin after a loading-time less than the time required to normally fill buckets 50A-C-D-E to full capacity, one of the two centrifuges 24A or 24B will be "ahead" of the other in terms of being loaded for centrifuging. As a result, there is a time-shift in the operational status of the two centrifuges 24A and 24B so that a high-priority STAT sample tube 20 may advantageously be shuttled to whichever of the two centrifuges 24A or 24B will be first-loaded and thus next-operated. This time differential thereby allows a STAT sample to begin and complete its centrifuging protocol, on average, in 50% less time than is required to fully load a bucket 50.

Figure 5:
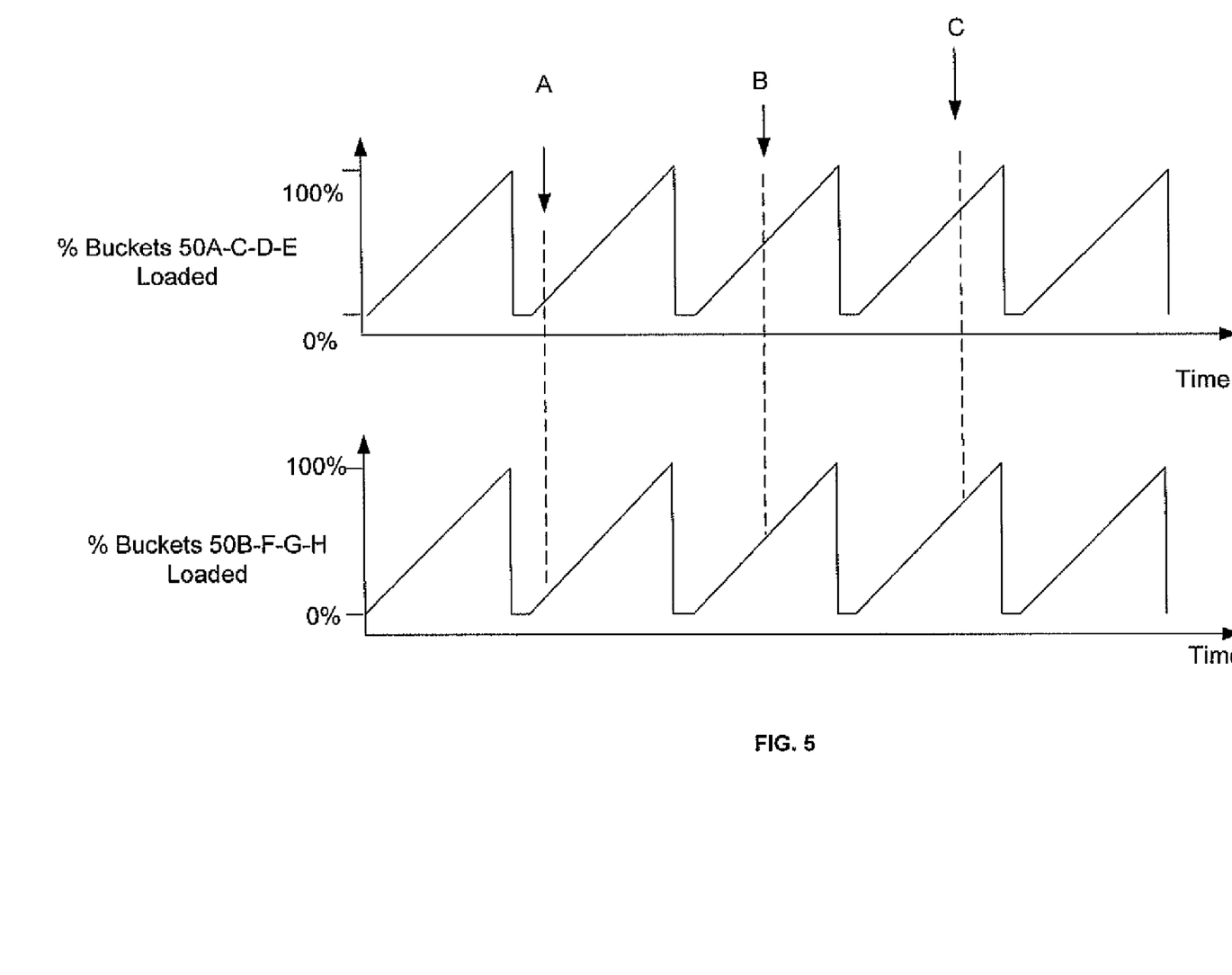
FIG. 5 is a timing plot of the prior art loading scheme of FIGS. 3-3D.
Figure 6:
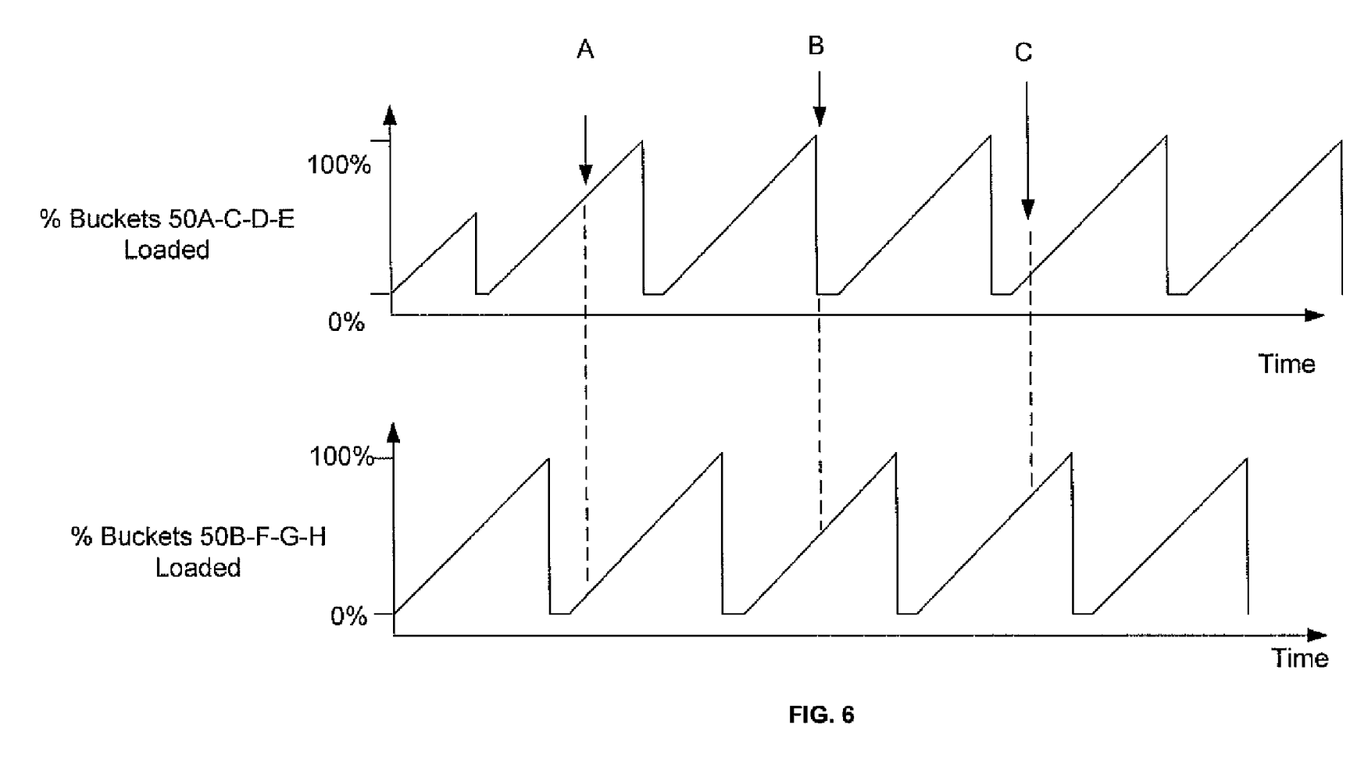
FIG. 6 is a timing plot of the present invention loading scheme of FIGS. 4A-4D.

This STAT processing advantage may also be illustrated by comparing the timing diagrams of centrifuge loading scheme of the prior art as depicted in FIG. 5 with the centrifuge loading scheme of the present invention as depicted in FIG. 6. In FIG. 5, buckets 50A, 50C, 50D and 50E on bucket loading platform 52 and buckets 5B, 50F, 50G and 50H on bucket loading platform 58 are filled to 100% of capacity in the alternating "odd-even" prior art loading scheme. If a STAT sample tube 20 appears at point "A", when minimal loading of any of buckets 50A-H has taken place, a relatively greater amount of time must lapse before the STAT tube can be placed in a bucket 50A-H to be spun by either centrifuge 24A or 24B. If a STAT sample tube 20 appears at point "B", when about 50% or half of any bucket 50A-H has taken place, an amount of time required for "half-loading" must lapse before bucket 50A-H can be placed in a centrifuge 24A or 24B for centrifuging. If a STAT sample tube 20 appears at point "C", when a greater loading of any buckets 50A-H has taken place, a relatively smaller amount of time must lapse before the bucket 50 holding the STAT sample tube 20 can be placed in a centrifuge 24A or 24B for centrifuging. In general, then, when the experience of a large number of STAT sample tubes 20 is evaluated, point B will be the norm and a "half-loaded" amount of time must lapse before the STAT tube 20 can be placed in any bucket 50A-H before being transferred to either centrifuge 24A or 24B for centrifuging. In this prior art loading scheme, regardless of whether a STAT sample tube 20 is placed in one of buckets 50A-C-D-E or buckets 50C-F-G-H, a STAT sample tube 20 will experience the same time lapse before the STAT sample can be centrifuged.

FIG. 6 illustrates the reduction in time lapse before the STAT sample tube 20 can be placed in a centrifuge 24A or 24B for centrifuging achieved by the present invention. In accord with the present invention, with only less-than or half-loaded buckets 50 used in the initial loading of centrifuge 24A, centrifuge 24A begins processing sample tubes 20 a shorter amount of time before centrifuge 24B begins processing sample tubes 20. In particular, as previously described, at least the first two buckets 50A-C are less than or about half-loaded with sample tubes 20 and then placed onto centrifuge 24A for centrifuging. Consequently, there is a time-shift in the operational status of centrifuges 24A and 24B so that whenever a STAT sample tube 20 appears, the STAT sample tube 20 may be advantageously shuttled to which ever of the two centrifuges 24A or 24B is in a most closely filled situation and most immediately available for centrifuging. For example if a STAT sample tube 20 appears at point "A", centrifuge 24A is much more closely ready for centrifuging than is centrifuge 24B and so the STAT sample tube 20 would be sent to centrifuge 24A. If a STAT sample tube 20 appears at point "B", centrifuge 24A is basically at the beginning of a loading process and so the STAT sample tube 20 would advantageously be sent to centrifuge 24B for centrifuging. Finally, if a STAT sample tube 20 appears at point "C", centrifuge 24B is nearly filled for centrifuging and so the STAT sample tube 20 would advantageously be sent to centrifuge 24B for centrifuging. As a benefit of the present invention, STAT sample tubes 20 will, on average, be presented for centrifuging with a processing delay that is about 50% less than STAT tubes 20 that are centrifuged using loading procedures that are currently practiced.

It should be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. For example, as described, either two buckets 50A and 50C or four buckets 50A-C-D-E may be initially less-than or about half-loaded to achieve the reduction in delay of processing a STAT sample tube 20. Further, only two centrifuges have been used in this illustration even though the STAT processing time advantage may be increased by the inclusion of a third centrifuge. Furthermore, for purposes of simplicity in describing the present invention, two sample loading stations 46 and 56 have been employed even though a single sample loading station may be adapted to perform the tasks of both sample loading stations 46 and 56.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A method of minimizing high priority STAT sample processing times during operation of a laboratory automation system having a conveyor for transporting individual sample tubes from a sample loading/unloading station to either of at least two centrifuges, the centrifuges having known centrifuging capacities, the method comprising the steps of:

initially loading a first one of said at least two centrifuges to a centrifuging capacity that is less than or about half of full centrifuging capacity;

commencing an operation cycle of said first centrifuge and, after the operation cycle of said first centrifuge is complete, refilling said first centrifuge to full capacity;

initially loading a second one of said at least two centrifuges to a centrifuging capacity that is about full centrifuging capacity;

commencing operation of said second centrifuge and, after the operation cycle of said first centrifuge is complete, refilling said second centrifuge to full capacity;

repeating the full loading and operation of said at least two centrifuges; and supplying high priority STAT samples to whichever of said at least two centrifuges is most closely filled to full capacity.

2. The procedure of claim 1 wherein loading said first centrifuge comprises placing samples in one or more pairs of buckets in a weight balanced pattern.

3. The procedure of claim 1 wherein loading said second centrifuge comprises placing samples in two or more pairs of buckets in a weight balanced pattern.

* * * * *